United States Patent [19]

Stivala

[11] Patent Number: 4,539,990

[45] Date of Patent: Sep. 10, 1985

[54] SUTURELESS CLOSURE SYSTEM

[76] Inventor: Oscar G. Stivala, 10 Whited St., Little Falls, N.Y. 13365

[21] Appl. No.: 532,702

[22] Filed: Sep. 16, 1983

[51] Int. Cl.³ ............................................. A61B 17/08
[52] U.S. Cl. .................................... 128/335; 128/337
[58] Field of Search ........................ 128/334, 335, 337

[56] References Cited

U.S. PATENT DOCUMENTS

| | | | |
|---|---|---|---|
| 2,303,131 | 11/1942 | Morgan | 128/335 |
| 2,371,978 | 3/1945 | Perham | 128/335 |
| 3,525,340 | 8/1970 | Gilbert | 128/337 |
| 3,926,193 | 12/1975 | Hasson | 128/335 |

*Primary Examiner*—Dalton L. Truluck
*Attorney, Agent, or Firm*—Bruns and Wall

[57] ABSTRACT

A sutureless closure system having fabric backed plates positioned along the side edges of a wound. Arcuate shaped clips bridge the wound between plates. Each clip contains a downwardly extended pin at each end which penetrates the fabric, but not the skin, to form a secure anchor for the bridge. Each clip is further formed of a bendable material so that the chordal length of the bridge can be shortened in assembly to tighten the system.

6 Claims, 6 Drawing Figures

U.S. Patent Sep. 10, 1985 4,539,990
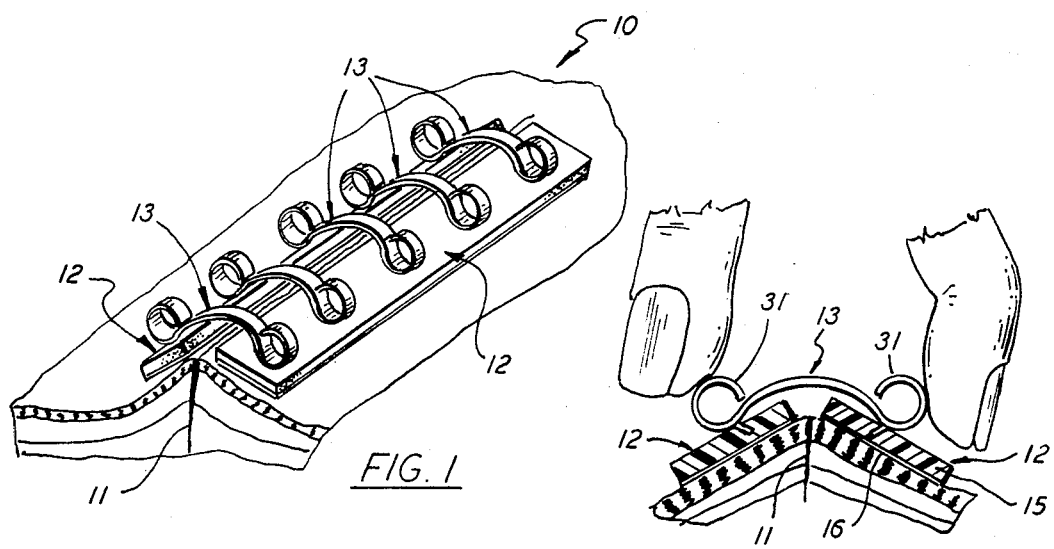
FIG. 1
FIG. 2
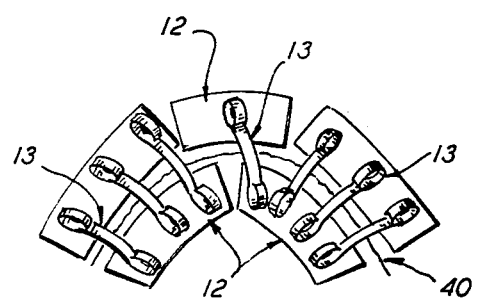
FIG. 4
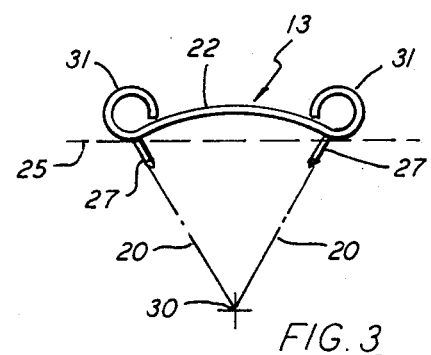
FIG. 3
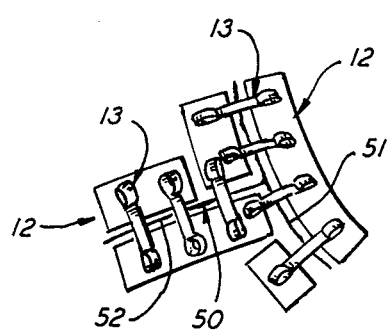
FIG. 5
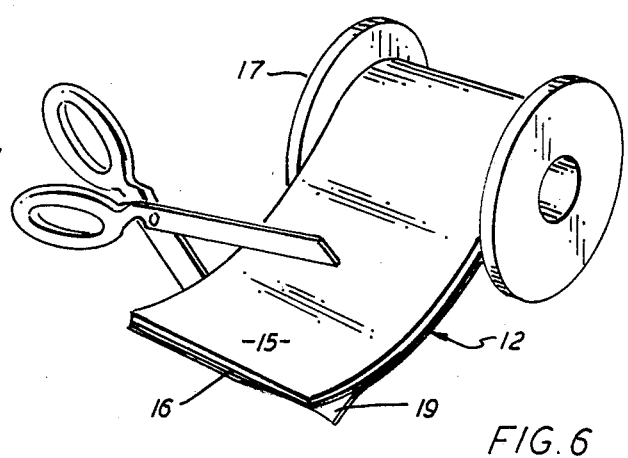
FIG. 6

SUTURELESS CLOSURE SYSTEM

BACKGROUND OF THE INVENTION

This invention relates to a sutureless closure for drawing together and retaining the edges of a wound or surgical incision.

Sutureless closures are well known in the art and have been used for some time to close wounds of various types. In most applications, the closure involves a pair of separate tapes, each having an adhesive backing so that the tapes can be attached to the skin on both sides of the wound. The tapes are cojoined by some type of connector to create a system for closing the wound and retaining it in this condition as it heals. Because the skin is not penetrated by the closure, no anesthesia is needed to install the system so long as the laceration is clean and does not require debridement. The system generally can be left in place longer than a suture system without having to compromise good cosmetic results and typically the sutureless system allows for easy access to the wound.

In one prevalent form of sutureless closure system, the adhesive tapes are joined by means of thread that is passed back and forth over the wound and which is somehow sewn into the tapes to close the system. Systems in which thread is used as the connecting element are shown in U.S. Pat. Nos. 345,541; 1,428,495; 1,969,188; 2,196,296 and 2,303,131. In all these systems, the thread lies very close to the skin in the wound area and can actually contact the wound particularly where swelling occurs. Consequently, the thread can pose a potential source of harm and/or infection at the laceration site. Sewing or tying the thread into the adhesive strips is also a relatively difficult task for the physician because of the lack of body provided by tape strips.

In a second type of sutureless closure system, elastic bands are utilized to cojoin adhesive backed strips and thus apply a constant closing force on the wound. In U.S. Pat. No. 2,018,517 a one piece elastic bandage is disclosed in which a gauze pad is placed under the center section thereof to cover and protect the wound area. This arrangement, of course, does not allow for ready access to the wound and also tends to apply pressure directly upon the wound rather than on the relatively undamaged edge regions. In U.S. Pat. Nos. 363,538 and 3,103,218, adhesive tapes positioned on both sides of the wound are provided with either vertically or horizontally disposed posts over which rubber bands are pasted. Here again the connecting elements lie close to, if not in actual contact with, the wound and require special attaching fixtures to hold the bands in place. The bands are not easily sterilized and are susceptible to breaking when exposed to water or the like.

Hasson in U.S. Pat. Nos. 3,698,395; 3,926,193 and 3,971,384 describes a number of different sutureless closure systems in which adhesive tapes are drawn together by means of a complex adjusting mechanism. For the most part, the Hasson mechanisms involve a ratchet-like device situated upon one tape that slidably engages a locking pawl seated upon an opposing tape. The pressure exerted by the system on the wound is adjusted by controlling the depth of penetration of the pawl into the ratchet. In a second embodiment, a bead chain is used to connect the tapes. One end of the chain is anchored on one tape and the chain adjustably received in a slotted passage carried on an opposing tape. In both cases, the adjusting mechanism is extremely complex and bulky. It is thus costly to manufacture and difficult to wear beneath clothing. Securing the adjustable components to the tapes poses special manufacturing problems and, in the case of the ratchet mechanism, alignment of the coacting parts present problems for the physician at the time of installation.

In U.S. Pat. No. 2,409,261 to Dow a series of wire connectors are placed under the tapes and are joined directly over the wound by twisting the wire ends together. By tightening the twists, the tapes can be drawn closer together. However, at the same time, the twisted wire is being shortened and thus driven down directly into the wound. Any amount of swelling in this area will cause the wire to become embedded in the wound where it can cause serious harm. The twisted wire ends also can easily catch or snap upon objects and the tapes are thus torn away from the skin causing the wound to reopen.

Kawehitch in U.S. Pat. No. 3,983,878 uses an elongated spring to draw a pair of specially prepared adhesive backed tapes together. The tapes, as well as the spring are complex and thus costly to manufacture. The spring, being a relatively rigid elongated member, presents alignment problems at the time of installation and because of the spring's special geometry is limited as to the areas in which it can be installed.

Many sutureless closures shown in the prior art do not evert the edges of the wound. Accordingly, good approximation of the skin layer alignment cannot be made which, quite often, produces infection or leads to eventual scarring.

SUMMARY OF THE INVENTION

It is therefore an object of the present invention to improve sutureless closure systems for closing wounds.

A further object of the present invention is to provide a sutureless closure system that is easy to install and adjust and which everts the edges of the wound to allow good alignment of the skin layers.

Yet another object of the present invention is to provide an inexpensive sutureless closure that can be easily adjusted to control the closing pressure exerted upon the wound.

A still further object of the present invention is to provide a sutureless closure that has raised connectors that bridge the wound and thus minimize the danger of infection.

Another object of the present invention is to provide a sutureless closure system that can be applied to any part of the body to accommodate irregular wounds or avulsion lacerations.

These and other objects of the present invention are attained by means of an adjustable sutureless closure system for drawing together and everting the side edges of a wound to help prevent infection and scarring that includes at least one pair of plates, each of which has a fabric-like backing material and a pressure sensitive adhesive underlayer whereby the plates can be attached to the skin on either side of the wound. The plates are connected by one or more arcuate shaped clips that bridge the wound. Pins are downwardly disposed from either end of each clip which penetrate the fabric layer on the underlying plates and thus securely anchor the clips in assembly. The pin length is less than the fabric depth so there is no danger of the pins penetrating the skin and causing harm. The clips are formed of a bendable material so that the chordal length between the end of the clip can be easily adjusted to set the holding pressure exerted by the system upon the wound.

BRIEF DESCRIPTION OF THE DRAWINGS

For a better understanding of these and other objects of the present invention, reference is had to the following detailed description of the invention which is to be read in conjunction with the accompanying drawings, wherein:

FIG. 1 is an enlarged view in perspective showing a sutureless closure system embodying the teachings of the present invention;

FIG. 2 is a side view in section of the system shown in FIG. 1 illustrating one of the connectors anchored between the coacting pair of plates;

FIG. 3 is a further enlarged side view of an adjustable connector used in the present system showing the geometry of the connector;

FIGS. 4 and 5 illustrate various system configurations wherein irregular shaped wounds are shown being retained by the system, and FIG. 6 is a perspective view showing a means for storing the plate material.

DESCRIPTION OF THE INVENTION

Referring initially to FIG. 1, there is shown a sutureless closure system, generally referenced 10, being used to close a straight incision 11 such as one made by a physician during surgery. Although the present system is ideally suited for closing surgical wounds of this nature, it has a great deal of flexibility and therefore can be installed to close any shape laceration found on almost any part of the body. In this arrangement, a coacting pair of plates 12—12 are attached to the skin along both side edges of the wound. The plates may be equal in length to the length of the wound or, alternatively, they may be cut slightly larger depending on the specific application. The plates in assembly are cojoined by means of a series of connectors or clips 13—13 that bridge the wound area.

With further reference to FIG. 2, the plates are of layered construction with each containing a fabric overlayer 15 and an adhesive underlayer 16. The term "fabric" as herein used refers to any material having a mesh-like finish or texture into which a pin can be inserted and once inserted held fast by the fabric to prevent lateral movement in any direction. Such fabrics can be made of a tightly woven textile or any number of cellular plastics that are readily available and inexpensive. The fabric is affixed to the underlayer by any suitable means to form a unitized structure. The outside surface of the underlayer is provided with a pressure sensitive adhesive that readily adheres to the skin to provide a strong long lasting bond therewith.

As shown in FIG. 6, the plate material can be sterilized and then packaged and stored upon a spool 17 for later use. A stripable release paper 19 is applied to the adhesive undercoating which can be peeled away immediately before applying the plate to the skin. The material sandwich is easily cut by scissors or the like from the spool. The material can be further trimmed to any desired size and/or shape needed to best fit the wound boundries.

The clips used to connect the plates are fabricated of a bendable material, such as metal or many forms of plastic, which can be adjusted as described below in assembly to control the holding pressure exerted upon the wound. Each clip, as shown in FIG. 3, is arcuate in form having an initial radius of curvature defined by radial lines 20—20. The curvature of the clip body 22 is sufficient to raise the center section of the body well above the chord 25 passing through the two ends of the clip. The clip thus forms a curved bridge that is capable of passing over the wound well above the lacerated area. A pair of downwardly disposed pins 27—27 are situated at both ends of the clip. Preferably, the pins and the clip are stamped from a single piece of material so that the pins are an integral part of the clip body. The pins, however, may be individually joined to the body by any suitable bonding process. The pins lie generally along radial lines 20—20 which pass through the center of curvature 30 of the clip. As a result of this construction the pins point downwardly and inwardly towards each other.

The two ends of the clip are also rolled over upon themselves to form finger engageable members 31—31. The members can be easily grasped by the physician between thumb and forefinger so that sufficient deforming pressure can be applied to bend the clip and thus vary its chordal length.

Referring back to FIG. 2, in assembly, the pins carried on each end of the clip are inserted into the fabric backing on opposed plates to securely anchor the clip on either side of the wound. The radial length of each pin is less than the depth of the fabric backing whereby the pins are prevented from penetrating the skin. Once installed, the physician simply has to grasp the end members as shown and bend the clip to a desired configuration with one hand while holding the wound edges closed with the other hand. All the clips in the system are tightened over the plates until some eversion of the skin is produced to provide a good approximation of the dermis and epidermis areas. Due to the inclination of the pins, a stronger anchorage is achieved when the clips are tightened in this manner thereby strengthening the system's holding force.

FIG. 4 shows the present closure system installed about a curved wound 40. In this case three plates are placed along the outside edge of the wound while two are placed along the inside edge. The clips are then evenly spaced between the inside and outside plates to apply a uniform holding pressure along the entire length of the wound. The plates have been trimmed to complement the wound and one plate on the inside edge of the wound is connected to two plates stationed along the outer edge.

FIG. 5 illustrates the system being used to close a T-shaped wound 50 having a first leg 51 and a second leg 52 running together to form right angle corners. Again the plates are trimmed to a desired size and shape to fit into the corner regions and are cojoined by clips. As illustrated, the clips in the corners are set to extend over both legs of the wound and adjusted to gain eversion of the skin in this difficult to close region.

As should now be evident, the present system may be left in place for longer periods of time than usually allowed with sutures or staples that penetrate the skin. In case of infection, one or more of the clips can be removed from the affected region without compromising the entire system. The wound can also be observed constantly since the plates do not shield the wound area. The system is easy to install and provide excellent cosmetic results without the need of plastic surgery. The system can be simply removed without the need of anesthesia which oftentimes is a problem with children and elderly people.

While this invention has been described with reference to the structure disclosed herein, it is not confined to the details set forth and this application is intended to cover any modifications or changes as may come within the scope of the following claims.

I claim:

1. A sutureless closure for drawing together the side margins of a wound and holding the margins closed in an everted condition that includes:

a pair of opposed anchor plates being located so that one of the plates is positioned on each side of the wound, each plate including a thick penetratable fabric having an adhesive layer affixed to the bottom surface thereof whereby the plate is securely attached to the skin adjacent the wound, an arcuate shaped bridge formed of a deformable metal, said bridge spanning the wound and overlying the two anchor plates so that the radius of curvature of the bridge is centered within the plane of the wound, a pin downwardly disposed from each end of the bridge, each pin penetrating the fabric of the underlying plate through the top surface of the plate, the length of the pins being less than the depth of the fabric whereby the pins cannot penetrate the skin, said pins slanting inwardly toward the center of the radius of curvature of the bridge whereby deforming the bridge inwardly to shorten the chordal length between the pins turns the plates upwardly and inwardly to evert the skin at wound opening.

2. The sutureless closure of claim 1 wherein the said fabric is formed of a cellular plastic material.

3. The sustreless closure of claim 1 wherein the bridge and the pins disposed therefrom are formed from a single piece of metal.

4. The sutureless closure of claim 1 wherein finger engageable members are located at each end of the bridge to facilitate deforming thereof.

5. The method of closing and everting a wound including the steps of adhering a fabric plate to the skin on both sides of the wound, spanning the wound between the plates with a deformable arcuate shaped bridge, pinning each end of the bridge into the approximate center of each plate with the pins slanting inwardly toward the wound to a depth that is less than the depth of the fabric whereby the pins will not penetrate the skin, deforming the bridge inwardly to shorten the chordal length thereof to turn the opposed plates inwardly and upwardly to evert the skin at the wound.

6. The method of claim 5 that further includes the step of shaping the opposed plates so that they complement the contour of the wound.

* * * * *